(12) United States Patent
Higuchi et al.

(10) Patent No.: US 11,090,007 B2
(45) Date of Patent: Aug. 17, 2021

(54) RESIDUAL ANAEROBIC WORK CAPACITY CALCULATING METHOD AND RESIDUAL ANAEROBIC WORK CAPACITY CALCULATING APPARATUS

(71) Applicant: NIPPON TELEGRAPH AND TELEPHONE CORPORATION, Tokyo (JP)

(72) Inventors: Yuichi Higuchi, Tokyo (JP); Koji Fujii, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 147 days.

(21) Appl. No.: 16/327,761

(22) PCT Filed: Aug. 30, 2017

(86) PCT No.: PCT/JP2017/031158
§ 371 (c)(1),
(2) Date: Feb. 22, 2019

(87) PCT Pub. No.: WO2018/043566
PCT Pub. Date: Mar. 8, 2018

(65) Prior Publication Data
US 2019/0231278 A1    Aug. 1, 2019

(30) Foreign Application Priority Data

Sep. 1, 2016  (JP) .................................. 2016-170594
Jan. 13, 2017  (JP) .............................. JP2017-004010

(51) Int. Cl.
A61B 5/00      (2006.01)
A61B 5/024     (2006.01)
(Continued)

(52) U.S. Cl.
CPC ............ *A61B 5/7278* (2013.01); *A61B 5/024* (2013.01); *A61B 5/0245* (2013.01); *A61B 5/224* (2013.01);
(Continued)

(58) Field of Classification Search
CPC .................................................... G16H 40/63
See application file for complete search history.

(56) References Cited

U.S. PATENT DOCUMENTS

2003/0013995 A1   1/2003   Oshima et al.
2011/0222668 A1   9/2011   Levenson
(Continued)

FOREIGN PATENT DOCUMENTS

CN        1389176 A       1/2003
CN      103025243 A       4/2013
(Continued)

OTHER PUBLICATIONS

Office Action received for Chinese Patent Application No. 201780052852.7, dated May 7, 2020, 14 pages (7 pages of English Translation and 7 pages of Office Action).
(Continued)

*Primary Examiner* — Scott Luan
(74) *Attorney, Agent, or Firm* — Womble Bond Dickinson (US) LLP

(57) ABSTRACT

A residual anaerobic work capacity calculating method includes a step (S1) of obtaining a heart rate, and a step (S2, S3) of calculating a residual anaerobic work capacity based on the obtained heart rate and a relationship between the residual anaerobic work capacity and the heart rate. This method need only measure the heart rate when calculating the residual anaerobic work capacity, and obviates the need to measure power by using an expensive power meter.

15 Claims, 6 Drawing Sheets

(51) Int. Cl.
- *A61B 5/22* (2006.01)
- *G16H 40/63* (2018.01)
- *A63B 69/16* (2006.01)
- *A63B 71/06* (2006.01)
- *A63B 69/00* (2006.01)
- *A61B 5/0245* (2006.01)

(52) U.S. Cl.
CPC ............ *A61B 5/4866* (2013.01); *A63B 69/00* (2013.01); *A63B 69/16* (2013.01); *A63B 71/06* (2013.01); *G16H 40/63* (2018.01); *A61B 2503/10* (2013.01); *A63B 2230/06* (2013.01)

(56) References Cited

U.S. PATENT DOCUMENTS

| | | | |
|---|---|---|---|
| 2011/0288381 | A1 | 11/2011 | Bartholomew et al. |
| 2013/0023739 | A1 | 1/2013 | Russell |

FOREIGN PATENT DOCUMENTS

| | | | |
|---|---|---|---|
| CN | 103815911 | A | 5/2014 |
| CN | 104056445 | A | 9/2014 |
| EP | 1127543 | A1 | 8/2001 |
| EP | 2575619 | A1 | 4/2013 |
| JP | 2013-529960 | A | 7/2013 |
| WO | 2011/149922 | A1 | 12/2011 |
| WO | 2016/103198 | A1 | 6/2016 |

OTHER PUBLICATIONS

Skiba, Philip Friere, "The Kinetics of the Work Capacity Above Critical Power", University of Exeter, Jun. 18, 2014, pp. 36-157.

Castillo et al., "Post-Exercise Blood Lactate Concentration and Maximal Accumulated Oxygen Deficit", Journal of Strength and Conditioning Research, vol. 25, Supplement 1, Mar. 2011, pp. S61.

Supplementary European Search Report and Search Opinion received for EP Patent Application No. 17846570.4, dated Apr. 2, 2020, 8 pages.

International Preliminary Report on Patentability received for PCT Patent Application No. PCT/JP2017/031158, dated Mar. 14, 2019, 12 pages (7 pages of English Translation and 5 pages of Original Document).

International Search Report and Written Opinion received for PCT Patent Application No. PCT/JP2017/031158, dated Dec. 5, 2017, 14 pages (7 pages of English Translation and 7 pages of Original Document).

Skiba, Philip Friere, "The Kinetics of the Work Capacity Above Critical Power", University of Exeter, Jun. 18, 2014, pp. 36, 37, 101-103, 156, 157.

Office Action received for Japanese Patent Application No. 2018-537348, dated Sep. 17, 2019, 10 pages (5 pages of English Translation and 5 pages of Office Action).

Skiba, Philip Friere, "The Kinetics of the Work Capacity Above Critical Power", University of Exeter, 2014, pp. 20 to 22, 36, pp. 37, 101 to 103, 138, pp. 142, 156 to 157.

RESIDUAL ANAEROBIC WORK CAPACITY CALCULATING METHOD AND RESIDUAL ANAEROBIC WORK CAPACITY CALCULATING APPARATUS

TECHNICAL FIELD

The present invention relates to a method and apparatus for calculating a residual anaerobic work capacity by using a heart rate.

BACKGROUND ART

In sports such as bicycle racing, an anaerobic work capacity is used as an index representing an athletic ability. More specifically, athletic abilities can be compared by measuring power given to a bicycle by a person via pedals by using a power meter attached to the bicycle, and estimating an anaerobic work capacity from the measured power.

For example, non-patent literature 1 discloses a method of estimating the residual amount of an anaerobic work capacity (to be referred to as "a residual anaerobic work capacity" hereinafter) when a person is exercising. This method disclosed in non-patent literature 1 can calculate the residual anaerobic work capacity from the power measured by the power meter.

Unfortunately, the method disclosed in non-patent literature 1 has the problem that the power meter which is a very expensive measurement device is necessary to measure the power.

RELATED ART LITERATURE

Non-Patent Literature

Non-Patent Literature 1: Skiba, Philip Friere (2014). The Kinetics of the Work Capacity Above Critical Power (Doctoral dissertation), University of Exeter, pp. 101-103 and pp. 156-157. Retrieved from http://ore.exeter.ac.uk/repository/handle/10871/15727

DISCLOSURE OF INVENTION

Problem to be Solved by the Invention

It is an object of the present invention to calculate the residual anaerobic work capacity without using any expensive power meter.

Means of Solution to the Problem

A residual anaerobic work capacity calculating method of the present invention includes a step of causing a processor to obtain a heart rate, and a step of causing the processor to calculate a residual anaerobic work capacity based on the obtained heart rate and a relationship between the residual anaerobic work capacity and the heart rate.

A residual anaerobic work capacity calculating apparatus of the present invention includes a heart rate obtaining unit configured to obtain a heart rate, and an arithmetic unit configured to calculate a residual anaerobic work capacity based on a relationship between the residual anaerobic work capacity and the heart rate, and the heart rate obtained by the heart rate obtaining unit.

Effect of the Invention

The present invention makes it possible to calculate the residual anaerobic work capacity without using any expensive power meter.

BEST MODE FOR CARRYING OUT THE INVENTION

Figure 1:
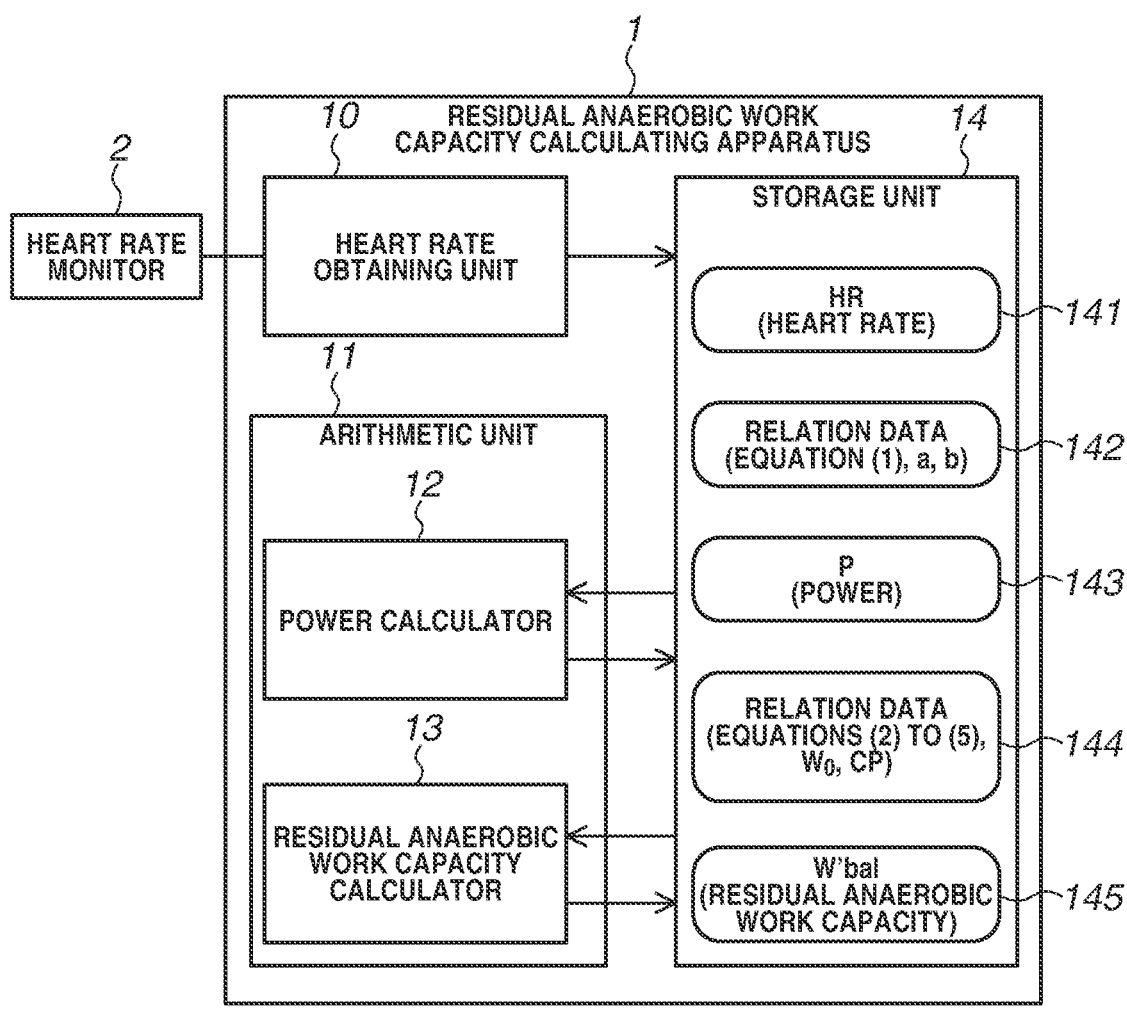
FIG. 1 is a block diagram of a residual anaerobic work capacity calculating apparatus according to the first embodiment of the present invention.

Embodiments of the present invention will be explained below with reference to the accompanying drawings. Note that in the following explanation, the same reference numerals denote constituent elements common to the embodiments, and a repetitive explanation thereof will be omitted.

First Embodiment

A residual anaerobic work capacity calculating apparatus 1 shown in FIG. 1 is, for example, an apparatus for estimating the residual anaerobic work capacity of a person who is exercising from his or her heart rate. The residual anaerobic work capacity calculating apparatus 1 can be implemented as one functional unit of a wearable device for measuring the biological information of a person wearing the device. The residual anaerobic work capacity calculating apparatus 1 is attached together with a heart rate monitor 2 for measuring the heart rate to, for example, the body of a person who is performing an anaerobic work such as bicycle racing, and calculates the residual anaerobic work capacity in real time based on the heart rate measured by the heart rate monitor 2.

As shown in FIG. 1, the residual anaerobic work capacity calculating apparatus 1 includes a heart rate obtaining unit 10, an arithmetic unit 11, and a storage unit 14.

The heart rate obtaining unit 10 is a functional unit for sequentially obtaining data of the heart rate which is measured by the heart rate monitor 2 attached to a human body or the like, and is output from the heart rate monitor 2 at a predetermined time interval (for example, an interval of 1 sec). Heart rate data 141 obtained by the heart rate obtaining unit 10 are sequentially stored in the storage unit 14. Note that data exchange between the residual anaerobic work capacity calculating apparatus 1 and the heart rate monitor 2 can be performed by either wired communication or wireless communication, i.e., the data exchanging method is not particularly limited. Note also that the heart rate data 141 can directly be input from the heart rate monitor 2 to the residual anaerobic work capacity calculating apparatus 1 as described above, but the heart rate data 141 measured by the heart rate monitor 2 may also be stored once in an internal storage device of a terminal such as a personal computer, and read out from the storage device by the residual anaerobic work capacity calculating apparatus 1 after that.

The storage unit 14 is a functional unit for storing various parameters pertaining to relations for calculating the residual anaerobic work capacity (to be described later), in addition to the heart rate data 141 described above.

The arithmetic unit 11 is a functional unit for calculating the residual anaerobic work capacity based on the heart rate data 141 obtained by the heart rate obtaining unit 10, and the relationship between the residual anaerobic work capacity and heart rate. More specifically, the arithmetic unit 11 includes a power calculator 12 and a residual anaerobic work capacity calculator 13.

The power calculator 12 is a functional unit for calculating the power from the heart rate. The "power" herein mentioned is power which a person gives to an operation target. In this embodiment, the "power" is explained as power which a person pedaling a bicycle gives to the bicycle as an example.

The power and heart rate have a correlation. For example, the relationship between power P and a heart rate HR can be represented by a linear equation as indicated by equation (1).

$$P = a \times HR + b \quad (1)$$

In equation (1), "a" and "b" are values which change from one person to another as a residual anaerobic work capacity calculation target.

The following method is an example of the method of calculating the relation representing the relationship between the heart rate and power. For example, the relation representing the relationship between the heart rate and power can be calculated by obtaining a calibration curve by the Conconi Test or the like. It is also possible to calculate the relation from a calibration curve obtained by measuring the power and heart rate during exercise and statistically analyzing the measured values. In this case, it is possible to measure the power by using a power meter, or indirectly obtain power data by measuring the speed in a state in which the relationship between the speed and power is already known such as bicycle trainer.

In the residual anaerobic work capacity calculating apparatus 1 of this embodiment, the relation representing the relationship between the heart rate and power obtained by the above method is stored in the storage unit 14 in advance. For example, equation (1) representing the relationship between the heart rate and power and the values of the parameters "a" and "b" are stored as relation data 142 in the storage unit 14 in advance. The power calculator 12 calculates the power based on equation (1), "a", and "b" stored in the storage unit 14, and the heart rate data 141 obtained by the heart rate obtaining unit 10. The power is calculated for each of sequentially obtained heart rates. Data 143 of the calculated power are sequentially stored in the storage unit 14, and used in arithmetic processing performed by the residual anaerobic work capacity calculator 13 (to be described below).

The residual anaerobic work capacity calculator 13 is a functional unit which calculates a residual anaerobic work capacity W'bal based on the relationship between the power and the residual anaerobic work capacity, and the power calculated by the power calculator 12.

As described in non-patent literature 1, the relationship between the residual anaerobic work capacity W'bal and the power P can be represented by equations (2) to (5).

$$W'bal = W_0 - \int_0^t W'_{EXP} e^{\frac{t-u}{\tau}} du \quad (2)$$

$$W'_{EXP} = \begin{cases} P - CP & (P > CP) \\ 0 & (P \leq CP) \end{cases} \quad (3)$$

$$\tau = 546 \exp(-0.01 D_{CP}) + 316 \quad (4)$$

$$D_{CP} = CP - P_{avg} \quad (5)$$

In equation (2), "$W_0$" is an anaerobic work capacity, each of "t" and "u" is time, and "$\tau$" is a time constant according to the recovery of the anaerobic work capacity $W_0$.

"$W'_{EXP}$" is a consumed anaerobic work amount. As indicated by equation (3), letting "P" be the power and "CP" be a critical power, the anaerobic work amount $W'_{EXP}$ is "P–CP" if the power P at that time is higher than the critical power CP, and is "0" if the power P at that time is lower than the critical power Cp. Note that the critical power CP is a maximum power which can be sustained for a long time without fatigue.

The time constant $\tau$ can be represented by equation (4). In equation (4), "$D_{CP}$" is the difference between an average value $P_{avg}$ of the power P and the critical power CP when the power P is equal to or lower than the critical power CP, and can be represented by equation (5).

As indicated by equations (2) to (5) above, the residual anaerobic work capacity W'bal is represented as a function of the power P. On the other hand, the power P can be represented as a function of the heart rate HR as indicated by equation (1). Accordingly, the residual anaerobic work capacity W'bal can be calculated from the measured heart rate HR by using equations (1) to (5).

Data of the anaerobic work capacity $W_0$ and the critical power CP contained in equations (1) to (5) must be obtained in advance. It is generally known that the relationship between the anaerobic work capacity $W_0$ and the critical power CP is represented by equation (6).

$$P = \frac{W_0}{t_{lim}} + CP \quad (6)$$

In equation (6), "$t_{lim}$" is a maximum duration. When a person keeps pedaling a bicycle with the same power P, the maximum duration $t_{lim}$ is inversely proportional to the power P. For a person as a measurement target of the residual anaerobic work capacity, therefore, the values of "$W_0$" and "CP" can be obtained by measuring the duration $t_{lim}$ at the power P at each of two points equal to or higher than the critical power CP, and solving two equations obtained by substituting the values of two sets of the measured power P and the duration $t_{lim}$ into equation (6).

Equations (2) to (5) representing the anaerobic work capacity $W_0$ and the critical power CP thus calculated and the relationship between the residual anaerobic work capacity W'bal and the power P are prestored as relation data 144 in the storage unit 14.

Based on the relation data 144 prestored in the storage unit 14 and the power P calculated by the power calculator 12, the residual anaerobic work capacity calculator 13 calculates the residual anaerobic work capacity W'bal and stores it as data 145 of the residual anaerobic work capacity in the storage unit 14.

Figure 2:
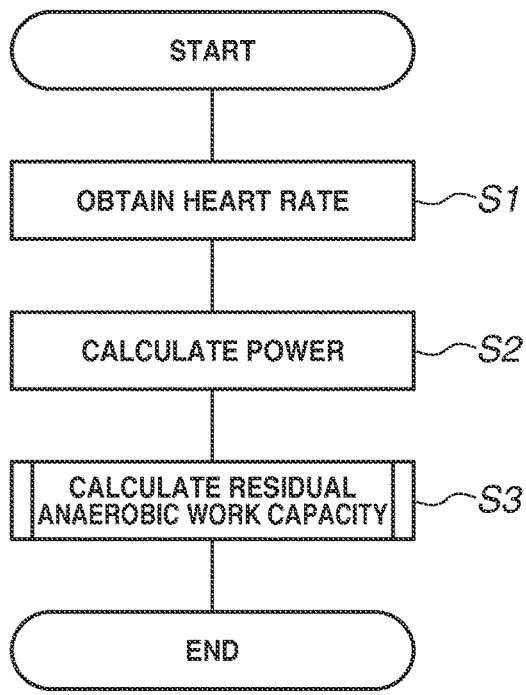
FIG. 2 is a flowchart showing the procedure of a residual anaerobic work capacity calculating process performed by the residual anaerobic work capacity calculating apparatus shown in FIG. 1.

Next, the procedure of the residual anaerobic work capacity calculating process performed by the residual anaerobic work capacity calculating apparatus 1 shown in FIG. 1 will be explained with reference to FIG. 2.

In the residual anaerobic work capacity calculating apparatus 1, the heart rate obtaining unit 10 first obtains, for example, the measured value of the heart rate from the heart rate monitor 2, and stores the value (heart rate HR) in the storage unit 14 (step S1). Then, the power calculator 12 reads out the latest heart rate HR and equation (1) from the storage unit 14, calculates the power P by substituting the heart rate HR into equation (1), and stores the power P in the storage unit 14 (step S2).

Subsequently, the residual anaerobic work capacity calculator 13 calculates the residual anaerobic work capacity W'bal based on the power P calculated in step S2 and equations (2) to (5) (step S3).

Figure 3:
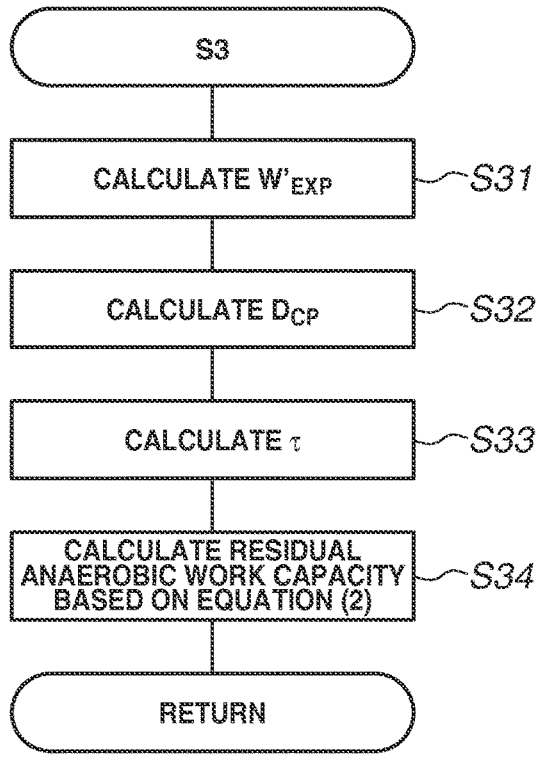
FIG. 3 is a flowchart showing the procedure of processing in step S3 of FIG. 2.

More specifically, as shown in FIG. 3, the residual anaerobic work capacity calculator 13 first reads out the latest power P, the critical power CP, and equation (3) from the storage unit 14, and calculates the consumed anaerobic work amount W'$_{EXP}$ by calculating equation (3) by using the power P and the critical power CP (step S31).

Also, the residual anaerobic work capacity calculator 13 further reads out the power P in the past obtained in past processing from the storage unit 14, and calculates the power average value P$_{avg}$ when the power P is equal to or lower than the critical power CP by using the past power P and the latest power P. In this calculation, it is possible to use all the past power P or a predetermined number of values of the past power P in order from the newest one. Then, the residual anaerobic work capacity calculator 13 reads out equation (5) from the storage unit 14, and calculates the difference D$_{CP}$ between the power average value P$_{avg}$ and the critical power CP based on equation (5) (step S32).

Subsequently, the residual anaerobic work capacity calculator 13 reads out equation (4) from the storage unit 14, and calculates equation (4) by using the difference D$_{CP}$ calculated in step S32, thereby calculating the time constant τ (step S33). After that, the residual anaerobic work capacity calculator 13 reads out the anaerobic work capacity $W_0$ and equation (2) from the storage unit 14, calculates the residual anaerobic work capacity W'bal by calculating equation (2) by using the anaerobic work amount W'$_{EXP}$ calculated in step S31 and the time constant τ calculated in step S33, and stores the residual anaerobic work capacity W'bal in the storage unit 14 (step S34).

The residual anaerobic work capacity data 145 stored in the storage unit 14 can be transmitted to, for example, an external device by wireless or wired communication, and can also be displayed on the screen of a display device (not shown) included in the residual anaerobic work capacity calculating apparatus 1.

As described above, the residual anaerobic work capacity calculating apparatus 1 shown in FIG. 1 can estimate the residual anaerobic work capacity based on the measured heart rate, and the data of the anaerobic work capacity $W_0$ and the critical power CP and the relationship between the residual anaerobic work capacity and the heart rate (equations (1) to (5)) prestored in the storage unit 14. That is, the residual anaerobic work capacity calculating apparatus 1 need only measure the heart rate when calculating the residual anaerobic work capacity, and this obviates the need to measure the power by using an expensive power meter.

Second Embodiment

A residual anaerobic work capacity calculating apparatus 1A shown in FIG. 4 differs from the residual anaerobic work capacity calculating apparatus 1 shown in FIG. 1 in that the residual anaerobic work capacity calculating apparatus 1A calculates the ratio of a residual anaerobic work capacity (to be referred to as "a residual anaerobic work capacity ratio" hereinafter) to an anaerobic work capacity without converting the heart rate into the power. More specifically, the residual anaerobic work capacity calculating apparatus 1A includes an arithmetic unit 11A including a residual anaerobic work capacity calculator 13A for calculating the residual anaerobic work capacity ratio to the anaerobic work capacity.

As disclosed in non-patent literature 1 described earlier, there is equation (7) as another approximation for estimating the residual anaerobic work capacity.

$$W'(t) = W_0 - (W_0 - W'(u))e^{-\frac{KD_{CP}}{W_0}(t-u)} \quad (7)$$

Equation (7) indicates the relationship between the residual anaerobic work capacity and power, and estimates a residual anaerobic work capacity W'(t) at time t from a residual anaerobic work capacity W'(u) at time u. In equation (7), "K" is a constant according to the recovery of an anaerobic work capacity $W_0$, and K=1 generally holds.

Equation (8) is derived by defining equation (7) indicating the relationship between the residual anaerobic work capacity and the power by the anaerobic work capacity $W_0$.

$$\frac{W'(t)}{W_0} = 1 - \left(1 - \frac{W'(u)}{W_0}\right)e^{-\frac{KD_{CP}}{W_0}(t-u)} \quad (8)$$

Letting "F" be the ratio of a residual anaerobic work capacity W' to the anaerobic work capacity $W_0$, equation (8) can be represented by equation (9).

$$F(t) = 1 - (1 - F(u))e^{-\frac{K(HR_{CP} - HR_{recovery})}{(HR_n - HR_{CP})t_{n\,lim}}(t-u)} \quad (9)$$

"HR$_{CP}$" is HR when power P is a critical power CP. HR will be explained as a heart rate in this specification, but a value obtained by converting a heart rate into a percentage may also be used as HR. "HR$_{recovery}$" is the average value of the heart rate HR when the power P is equal to or lower than the critical power CP, i.e., the average value of the heart rate HR equal to or lower than HR$_{CP}$. "HR$_n$" is a heart rate when a person exercises at a constant exercise intensity equal to or higher than $HR_{CP}$, and "$t_{nlim}$" is a maximum duration when a person exercises at a constant exercise intensity equal to or higher than $HR_{CP}$.

The relationship between a value $W_{OHR}$ obtained by converting the anaerobic work capacity $W_0$ by the heart rate HR, and $HR_{CP}$, $HR_n$, and $t_{nlim}$ can be represented by equation (10).

$$HR_n = \frac{W_{0HR}}{t_{n\,lim}} + HR_{CP} \quad (10)$$

"$W_{OHR} = (HR_n - HR_{CP})t_{nlim}$" is obtained by modifying equation (10). The value of $W_{OHR}$, i.e., the value of "$(HR_n - HR_{CP})t_{nlim}$" can be obtained by, for example, pedaling a bicycle at a constant exercise intensity for the maximum duration $t_{nlim}$.

$W_{OHR}$ can also be replaced with equation (11). In this case, equation (8) can be represented by equation (12) where "$\Delta t$" is a data interval.

$$W_{0HR} = \sum_{m=0}^{m=\frac{t_{n\,lim}}{\Delta t}} (HR_n - HR_{CP}) \quad (11)$$

$$F(t) = 1 - (1 - F(u))e^{\frac{K(HR_{CP} - HR_{recovery})}{\sum_{m=0}^{m=t_{n\,lim}/\Delta t}(HR_n - HR_{CP})}(t-u)} \quad (12)$$

Note that the value of $HR_{CP}$ can be estimated from equation (10), and can also be calculated from equation (13) below. In equation (13), "$HR_{max}$" is a maximum value of the heart rate, and "$HR_{min}$" is a minimum value of the heart rate.

$$HR_{CP} = (HR_{max} - HR_{min}) \times (70\% \sim 80\%) + HR_{min} \quad (13)$$

Of parameters contained in equation (9) above, data of a constant K, $HR_{CP}$, and "$(HR_n - HR_{CP})t_{nlim}$" are preobtained by the above-described method, and stored as relation data 146 in a storage unit 14 together with equation (9) or (12). In equation (13), "70% to 80%" is a general value, and this value sometimes changes for another person.

$HR_{recovery}$ is data calculated based on heart rate data 141 obtained by a heart rate obtaining unit 10. For example, the residual anaerobic work capacity calculator 13A calculates the average value of the heart rate HR equal to or lower than $HR_{CP}$ based on the sequentially obtained heart rate data 141, and stores the value as $HR_{recovery}$ data 147 in the storage unit 14.

The residual anaerobic work capacity calculator 13A calculates a ratio (residual anaerobic work capacity ratio) F(t) of the residual anaerobic work capacity W'(t) to the anaerobic work capacity $W_0$ by calculating equation (9) based on the relation data 146 stored in the storage unit 14 and the calculated value of $HR_{recovery}$, and stores the ratio F(t) as residual anaerobic work capacity ratio data 148 in the storage unit 14.

The procedure of the residual anaerobic work capacity calculating process performed by the residual anaerobic work capacity calculating apparatus 1A shown in FIG. 4 will be explained below with reference to FIG. 5.

In the residual anaerobic work capacity calculating apparatus 1A, like the residual anaerobic work capacity calculating apparatus 1 shown in FIG. 1, the heart rate obtaining unit 10 first obtains, for example, a measured value of the heart rate from a heart rate monitor 2, and stores the value (heart rate HR) in the storage unit 14 (step S1).

Figure 6:
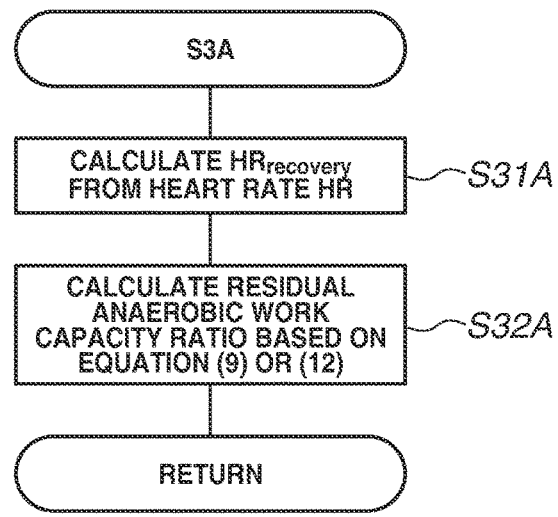
FIG. 6 is a flowchart showing the procedure of processing in step S3A of FIG. 5.

Then, the residual anaerobic work capacity calculator 13A calculates the ratio F(t) of the residual anaerobic work capacity W'(t) to the anaerobic work capacity $W_0$ based on the heart rate HR obtained in step S1 (step S3A). More specifically, as shown in FIG. 6, the residual anaerobic work capacity calculator 13A first reads out a past heart rate HR obtained in the past processing, the latest heart rate HR obtained in step S1, and $HR_{CP}$ from the storage unit 14, and calculates the average value $HR_{recovery}$ of the heart rates HR equal to or lower than $HP_{CP}$ (step S31A). In this step, it is possible to use all the past heart rates HR, or use a predetermined number of past heart rates HR in order from the newest one. Subsequently, the residual anaerobic work capacity calculator 13A reads out the values of K, $HR_{CP}$, and "$(HR_n - HR_{CP})t_{nlim}$" and equation (9) or (12) from the storage unit 14, calculates the residual anaerobic work capacity ratio F(t) by calculating equation (9) or (12) by using the value of $HR_{recovery}$ calculated in step S31A, and stores the residual anaerobic work capacity ratio F(t) in the storage unit 14 (step S32A).

The residual anaerobic work capacity ratio data 148 stored in the storage unit 14 can be, for example, transmitted to an external device by wireless or wired communication, and can also be displayed on the screen of a display device (not shown) included in the residual anaerobic work capacity calculating apparatus 1A.

Figure 4:
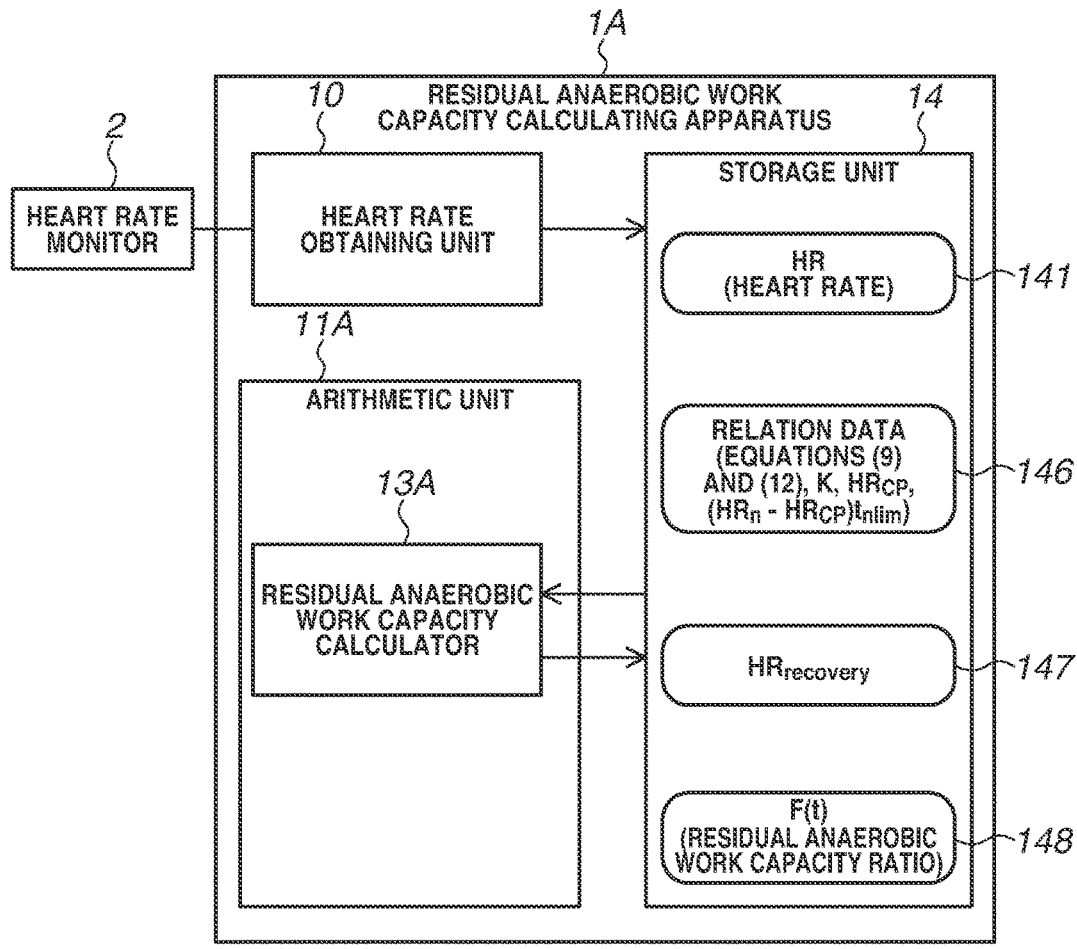
FIG. 4 is a block diagram of a residual anaerobic work capacity calculating apparatus according to the second embodiment of the present invention.
Figure 5:
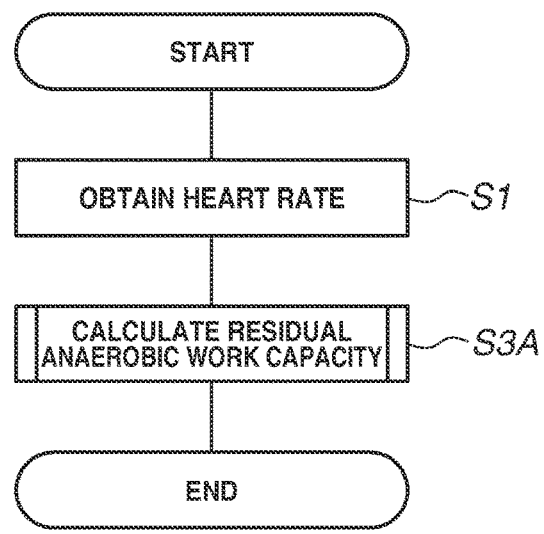
FIG. 5 is a flowchart showing the procedure of a residual anaerobic work capacity calculating process performed by the residual anaerobic work capacity calculating apparatus shown in FIG. 4.

Like the residual anaerobic work capacity calculating apparatus 1 shown in FIG. 1, the residual anaerobic work capacity calculating apparatus 1A shown in FIG. 4 can estimate the residual anaerobic work capacity based on the measured heart rate.

Also, the residual anaerobic work capacity calculating apparatus 1A calculates the residual anaerobic work capacity ratio F(t) by using a numerical formula (equation (9) or (12)) standardized by the anaerobic work capacity $W_0$. Accordingly, the residual anaerobic work capacity can be estimated without converting the heart rate into the power.

Furthermore, the values of various parameters such as K, $HR_{CP}$, and "$(HR_n - HR_{CP})t_{nlim}$" to be stored in the storage unit 14 in advance can be obtained by measuring the heart rate without using any power meter. This makes it possible to calculate the residual anaerobic work capacity with a lower cost.

Third Embodiment

Figure 7:
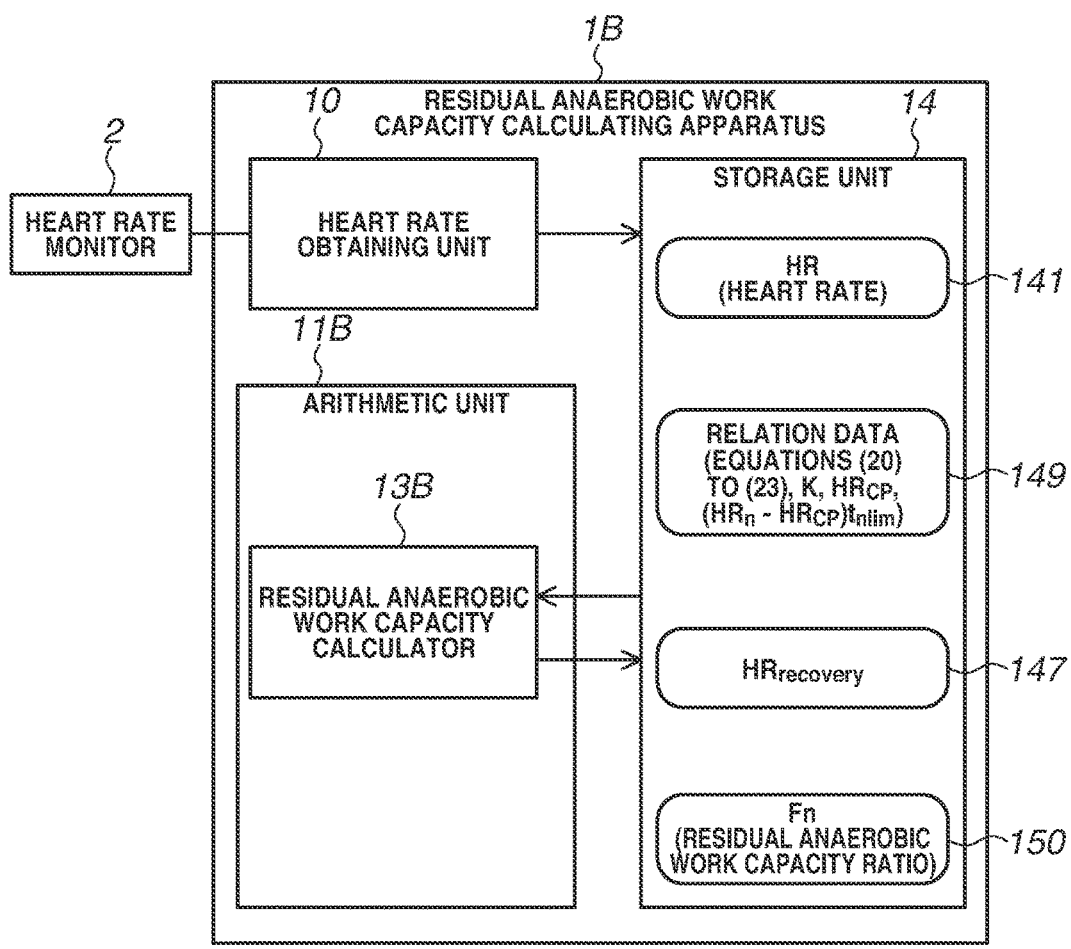
FIG. 7 is a block diagram of a residual anaerobic work capacity calculating apparatus according to the third embodiment of the present invention.

A residual anaerobic work capacity calculating apparatus 1B shown in FIG. 7 differs from the residual anaerobic work capacity calculating apparatus 1A shown in FIG. 4 in that the residual anaerobic work capacity calculating apparatus 1B calculates a residual anaerobic work capacity ratio based on a difference equation. More specifically, the residual anaerobic work capacity calculating apparatus 1B includes an arithmetic unit 11B including a residual anaerobic work capacity calculator 13B for calculating the residual anaerobic work capacity ratio based on a difference equation.

There are equations (14) and (15) as other approximations for estimating the residual anaerobic work capacity. Equation (14) is an approximation when P>CP, and equation (15) is an approximation when CP>P.

$$\frac{dW'}{dt} = -(P - CP) + K\left(1 - \frac{W'}{W_0}\right)D_{CP} \quad (14)$$

$$\frac{dW'}{dt} = K\left(1 - \frac{W'}{W_0}\right)D_{CP} \quad (15)$$

Equations (14) and (15) represent the relationship between the residual anaerobic work capacity and the power. The first term on the right side of equation (14) represents a used anaerobic work amount, and the second term represents the recovery amount of an anaerobic work capacity $W_0$.

Equations (16) and (17) can be obtained by standardizing equations (14) and (15) representing the relationship between the residual anaerobic work capacity and the power by using the anaerobic work capacity $W_0$. Equation (16) is an equation when P>CP, and equation (17) is an equation when CP>P.

$$\frac{d}{dt}\left(\frac{W'}{W_0}\right) = -\frac{(P - CP)}{W_0} + K\left(1 - \frac{W'}{W_0}\right)\frac{D_{CP}}{W_0} \quad (16)$$

$$\frac{d}{dt}\left(\frac{W'}{W_0}\right) = K\left(1 - \frac{W'}{W_0}\right)\frac{D_{CP}}{W_0} \quad (17)$$

Letting F be the ratio (the residual anaerobic work capacity ratio) of a residual anaerobic work capacity W' to the anaerobic work capacity $W_0$, equations (16) and (17) can be represented by equations (18) and (19), respectively. Equation (18) is an equation when P>CP, and equation (19) is an equation when CP>P.

$$\frac{d}{dt}(F) = -\frac{(HR - HR_{CP})}{(HR_n - HR_{CP})t_{n\,lim}} + K(1 - F)\frac{HR_{CP} - HR_{recovery}}{(HR_n - HR_{CP})t_{n\,lim}} \quad (18)$$

$$\frac{d}{dt}(F) = K(1 - F)\frac{HR_{CP} - HR_{recovery}}{(HR_n - HR_{CP})t_{n\,lim}} \quad (19)$$

Furthermore, equations (20) and (21) are obtained by representing equations (18) and (19) by difference equations. Equation (20) is an equation when P>CP, and equation (21) is an equation when CP>P.

$$F_n = \quad (20)$$
$$F_{n-1} - \frac{(HR - HR_{CP})}{(HR_n - HR_{CP})t_{n\,lim}}\Delta t + K(1 - F_{n-1})\frac{HR_{CP} - HR_{recovery}}{(HR_n - HR_{CP})t_{n\,lim}}\Delta t$$

$$F_n = F_{n-1} + K(1 - F_{n-1})\frac{HR_{CP} - HR_{recovery}}{(HR_n - HR_{CP})t_{n\,lim}}\Delta t \quad (21)$$

In equations (20) and (21), data of a constant K, $HR_{CP}$, and "$(HR_n - HR_{CP})t_{nlim}$" are obtained beforehand and stored as relation data 149 in a storage unit 14 together with equations (20) and (21), in the same manner as in the second embodiment.

Also, when using equation (11), equation (18) can be represented by equations (22) and (23), in the same manner as in the second embodiment. Equation (22) is an equation when P>CP, and equation (23) is an equation when CP>P. In addition, "$\Delta t$" is a data interval. Instead of equations (20) and (21), equations (22) and (23) can be prestored as the relation data 149 in the storage unit 14.

$$F_n = F_{n-1} - \frac{(HR - HR_{CP})}{\sum_{m=0}^{m=t_{n\,lim}/\Delta t}(HR_n - HR_{CP})}\Delta t + \quad (22)$$

$$K(1 - F_{n-1})\frac{HR_{CP} - HR_{recovery}}{\sum_{m=0}^{m=t_{n\,lim}/\Delta t}(HR_n - HR_{CP})}$$

$$F_n = F_{n-1} + K(1 - F_{n-1})\frac{HR_{CP} - HR_{recovery}}{\sum_{m=0}^{m=t_{n\,lim}/\Delta t}(HR_n - HR_{CP})}\Delta t \quad (23)$$

Like the residual anaerobic work capacity calculating apparatus 1A shown in FIG. 4, the residual anaerobic work capacity calculator 13B obtains data 147 of $HR_{recovery}$ by calculating the average value of heart rates HR equal to or lower than $HR_{CP}$.

The residual anaerobic work capacity calculator 13B calculates a residual anaerobic work capacity ratio Fn by calculating equation (17) or (18) by using the values of K, $HR_{CP}$, "$(HR_n - HR_{CP})t_{nlim}$" stored in the storage unit 14 and the calculated value of $HR_{recovery}$, and stores the calculated residual anaerobic work capacity ratio Fn as data 150 of the residual anaerobic work capacity ratio in the storage unit 14.

Figure 8:
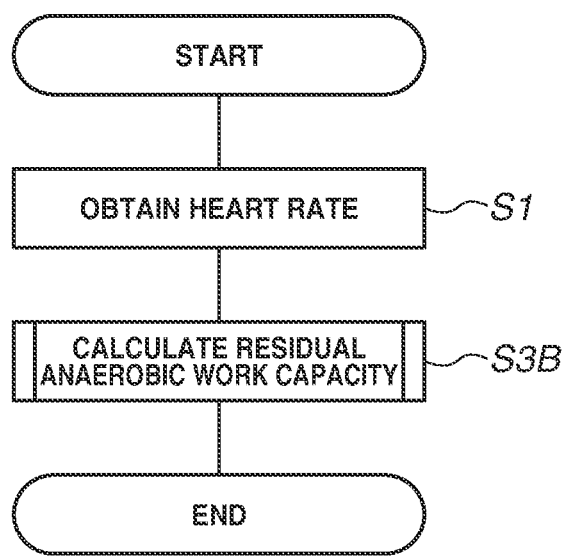
FIG. 8 is a flowchart showing the procedure of a residual anaerobic work capacity calculating process performed by the residual anaerobic work capacity calculating apparatus shown in FIG. 7.

The procedure of the residual anaerobic work capacity calculating process performed by the residual anaerobic work capacity calculating apparatus 1B shown in FIG. 7 will be explained below with reference to FIG. 8.

In the residual anaerobic work capacity calculating apparatus 1B, as in the residual anaerobic work capacity calculating apparatus 1 shown in FIG. 1, a heart rate obtaining unit 10 first obtains the measured value of the heart rate from, for example, a heart rate monitor 2, and stores the value (heart rate HR) in the storage unit 14 (step S1). Then, the residual anaerobic work capacity calculator 13B calculates the residual anaerobic work capacity ratio Fn based on the heart rate HR obtained in step S1 (step S3B).

Figure 9:
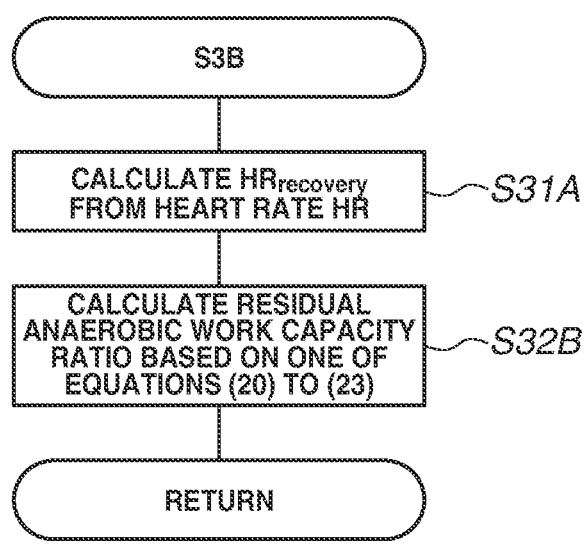
FIG. 9 is a flowchart showing the procedure of processing in step S3B of FIG. 8.

More specifically, as shown in FIG. 9, like the residual anaerobic work capacity calculator 13A, the residual anaerobic work capacity calculator 13B first calculates $HR_{recovery}$ based on a past heart rate HR, the latest heart rate HR, and $HR_{CP}$ (step S31A). Then, the residual anaerobic work capacity calculator 13B reads out the values of K, $HR_{CP}$, and "$(HR_n - HR_{CP})t_{nlim}$" and one of equations (20) to (23) from the storage unit 14, calculates the residual anaerobic work capacity ratio Fn by calculating one of equations (20) to (23) by using the value of $HR_{recovery}$ calculated in step S31A, and stores the calculated residual anaerobic work capacity ratio Fn in the storage unit 14 (step S32B).

The data 150 of the residual anaerobic work capacity ratio Fn stored in the storage unit 14 can be, for example, transmitted to an external device by wireless or wired communication, and can also be displayed on the screen of a display device (not shown) included in the residual anaerobic work capacity calculating apparatus 1B.

As described above, like the residual anaerobic work capacity calculating apparatus 1A shown in FIG. 4, the residual anaerobic work capacity calculating apparatus 1B shown in FIG. 7 calculates the residual anaerobic work capacity ratio Fn by using the numerical formula (one of equations (20) to (23)) standardized by the anaerobic work capacity $W_0$. Therefore, various parameters to be stored in the storage unit 14 in advance can be obtained by measuring the heart rate without using any power meter, so the residual anaerobic work capacity can be calculated with a lower cost.

In addition, the residual anaerobic work capacity calculating apparatus 1B uses the difference equation (one of equations (20) to (23)) as a numerical formula for calculating the residual anaerobic work capacity ratio Fn. This facilitates installing a program for calculating the residual anaerobic work capacity in the product.

<<Hardware Configuration>>

The functional units of the residual anaerobic work capacity calculating apparatus 1, 1A, or 1B shown in FIG. 1, 4, or 7 are implemented by the cooperation of software loaded into a computer and the hardware resources of the computer. As the computer, a portable terminal such as a smartphone can be used.

Figure 10:
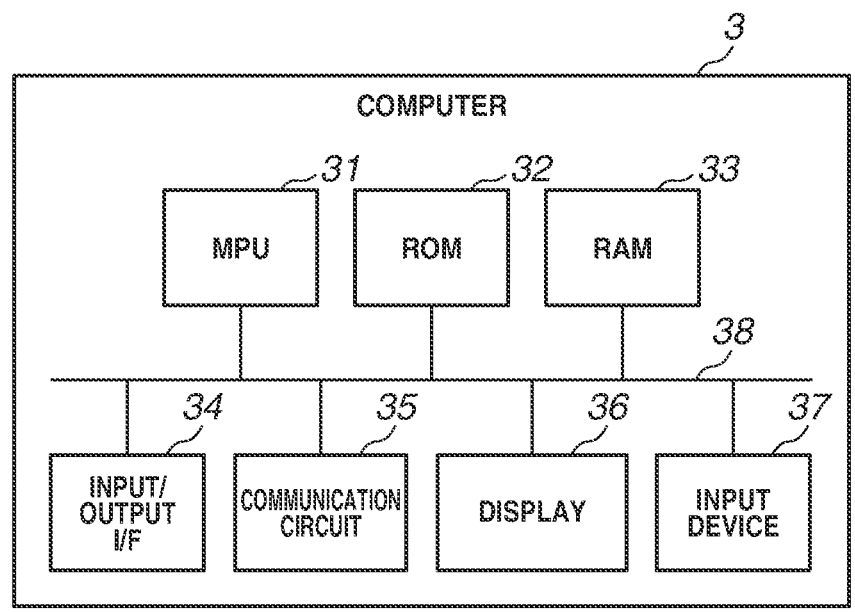
FIG. 10 is a block diagram showing the main hardware configuration of a computer.

FIG. 10 shows the main hardware configuration of the computer. A computer 3 includes an MPU (Micro-Processing Unit) 31, a ROM (Read Only Memory) 32, a RAM (Random Access Memory) 33, an input/output interface (I/F) 34, a communication circuit 35, a display 36, and an input device 37. These devices are connected via a bus 38.

The MPU 31 is a processor for controlling the operation of the whole computer 3. A CPU (Central Processing Unit) can also be used in place of the MPU 31.

The ROM 32 is a memory for storing an operating system, a control program to be executed by the computer 3, and various kinds of data. The control program includes a residual anaerobic work capacity calculation program for implementing the functional units of the residual anaerobic work capacity calculating apparatus 1, 1A, or 1B. When implementing the functional units of the residual anaerobic work capacity calculating apparatus 1 shown in FIG. 1, the ROM 32 stores the data 141 to 145. When implementing the functional units of the residual anaerobic work capacity calculating apparatus 1A shown in FIG. 4, the ROM 32 stores the data 141 and 146 to 148. When implementing the functional units of the residual anaerobic work capacity calculating apparatus 1B shown in FIG. 7, the ROM 32 stores the data 141, 147, 149, and 150.

The RAM 33 is a memory to be used as a work area of the MPU 31, and temporarily stores various kinds of data required to execute programs. When executing the residual anaerobic work capacity calculation program, the RAM 33 temporarily stores values obtained during the calculation of the residual anaerobic work capacity W'bal or the residual anaerobic work capacity ratios F(t) and Fn. When implementing the functional units of the residual anaerobic work capacity calculating apparatus 1 shown in FIG. 1, the RAM 33 stores the heart rate HR, the power P, the anaerobic work amount $W'_{EXP}$, the average value $P_{avg}$ of power, the difference $D_{CP}$ between the average value $P_{avg}$ of power and the critical power CP, the time constant $\tau$, and the residual anaerobic work capacity W'bal. When implementing the functional units of the residual anaerobic work capacity calculating apparatus 1A shown in FIG. 4, the RAM 33 stores the heart rate HR, the average value $HR_{recovery}$ of the heart rate HR, and the residual anaerobic work capacity ratio F(t). When implementing the functional units of the residual anaerobic work capacity calculating apparatus 1B shown in FIG. 7, the RAM 33 stores the heart rate HR, the average value $HR_{recovery}$ of the heart rate HR, and the residual anaerobic work capacity ratio Fn.

The input/output interface 34 is an interface for connecting a peripheral device to the computer 3, and is used to connect, for example, the heart rate monitor 2 to the computer 3 by wired connection. The communication circuit 35 is a device for exchanging data. The display 36 is formed by a touch panel or the like, and the input device 37 is formed by operation buttons or the like.

The MPU 31 implements the functional units of the residual anaerobic work capacity calculating apparatus 1, 1A, or 1B by reading out the residual anaerobic work capacity calculation program from the ROM 32, and controlling each unit of the computer 3 by operating in accordance with the program.

The invention made by the present inventors has been explained in detail above based on the embodiments, but the present invention is not limited to these embodiments, and various changes can of course be made without departing from the spirit and scope of the invention.

In each of the above embodiments, a case in which the process of calculating the residual anaerobic work capacity is implemented by program processing performed by the MPU or the like has been explained as an example. However, a dedicated hardware circuit may also implement a part or the whole of the above processing. For example, it is also possible to discretely configure the heart rate obtaining unit 10, power calculator 12, and the residual anaerobic work capacity calculator 13, 13A, or 13B by using programmable controllers. Also, each of the residual anaerobic work capacity calculating apparatuses 1, 1A, and 1B has been explained as a device different from the heart rate monitor 2, but the residual anaerobic work capacity calculating apparatus may also incorporate the heart rate monitor 2. In this case, the heart rate monitor 2 configures the heart rate obtaining unit 10.

INDUSTRIAL APPLICABILITY

The residual anaerobic work capacity calculating method and apparatus according to the present invention are widely applicable to techniques for obtaining and managing human biological information in not only bicycle racing but also general sports of performing anaerobic work.

EXPLANATION OF THE REFERENCE NUMERALS AND SIGNS 1, 1A, 1B . . . residual anaerobic work capacity calculating apparatus, 2 . . . heart rate monitor, 10 . . . heart rate obtaining unit, 11, 11A, 11B . . . arithmetic unit, 12 . . . power calculator, 13, 13A, 13B . . . residual anaerobic work capacity calculator, 14 . . . storage unit, 141 . . . heart rate data, 142, 144, 146, 149 . . . relation data, 143 . . . power data, 145 . . . residual anaerobic work capacity data, 147 . . . $HR_{recovery}$ data, 148, 150 . . . residual anaerobic work capacity ratio data

The invention claimed is:

1. A residual anaerobic work capacity calculating method comprising:
    a step of causing a processor to obtain a heart rate from a heart rate obtaining unit coupled to a heart rate monitor; and
    a step of causing the processor to calculate a residual anaerobic work capacity based on the obtained heart rate and a predetermined relationship between the residual anaerobic work capacity and the heart rate;
    using the calculated residual anaerobic work capacity to manage biological information for a body performing anaerobic work, when said body is connected to said heart rate monitor by transmitting the calculated residual anaerobic work capacity to an external device or displaying the calculated residual anaerobic work capacity on a display to compare athletic abilities by using the calculated residual anaerobic work capacity.

2. The residual anaerobic work capacity calculating method according to claim 1, wherein the step of causing the processor to calculate a residual anaerobic work capacity includes:
 a step of causing the processor to calculate power based on the obtained heart rate and a first relation indicating a relationship between the heart rate and the power; and
 a step of causing the processor to calculate the residual anaerobic work capacity based on the calculated power and a second relation indicating a relationship between the residual anaerobic work capacity and the power.

3. The residual anaerobic work capacity calculating method according to claim 2, wherein, letting W'bal be the residual anaerobic work capacity, $W'_0$ be an anaerobic work capacity, t and u be time, $\tau$ be a time constant according to recovery of the anaerobic work capacity $W_0$, $W'_{EXP}$ be a consumed anaerobic work amount, P be power, CP be critical power, and $P_{avg}$ be an average value of the power when the power is not more than the critical power, the second relation includes equations (A), (B), (C), and (D):

$$W'bal = W_0 - \int_0^t W'_{EXP} e^{\frac{t-u}{\tau}} du \qquad (A)$$

$$W'_{EXP} = \begin{cases} P - CP & (P > CP) \\ 0 & (P \le CP) \end{cases} \qquad (B)$$

$$\tau = 546\exp(-0.01 D_{CP}) + 316 \qquad (C)$$

$$D_{CP} = CP - P_{avg}. \qquad (D)$$

4. The residual anaerobic work capacity calculating method according to claim 1, wherein the step of causing the processor to calculate a residual anaerobic work capacity includes a step of causing the processor to calculate a ratio of the residual anaerobic work capacity to an anaerobic work capacity based on a relation in which a relationship between the residual anaerobic work capacity and the power is standardized by the anaerobic work capacity, and the obtained heart rate.

5. The residual anaerobic work capacity calculating method according to claim 4, wherein, letting F be the ratio of the residual anaerobic work capacity to the anaerobic work capacity, t and u (u<t) be time, $\Delta t$ be a data interval, K be a coefficient according to recovery of an anaerobic work capacity $W_0$, $HR_{CP}$ be the heart rate when power is critical power, $HR_{recovery}$ be an average value of the heart rate when the power is not more than the critical power, $HR_n$ be the heart rate when a person exercises at a constant exercise intensity not less than $HR_{CP}$, and $t_{nlim}$ be a maximum duration when a person exercises at the constant exercise intensity, the relation is represented by one of equations (E) and (E'):

$$F(t) = 1 - (1 - F(u))e^{\frac{K(HR_{CP} - HR_{recovery})}{(HR_n - HR_{CP})t_{n\,lim}}(t-u)} \qquad (E)$$

$$F(t) = 1 - (1 - F(u))e^{\frac{K(HR_{CP} - HR_{recovery})}{\sum_{m=0}^{m=t_{n\,lim}/\Delta t}(HR_n - HR_{CP})}(t-u)} \qquad (E')$$

6. The residual anaerobic work capacity calculating method according to claim 4, wherein, letting F be the ratio of the residual anaerobic work capacity to the anaerobic work capacity, t and u (u<t) be time, $\Delta t$ be a data interval, K be a coefficient according to recovery of an anaerobic work capacity $W_0$, $HR_{CP}$ be the heart rate when power is critical power, $HR_{recovery}$ be an average value of the heart rate when the power is not more than the critical power, $HR_n$ be the heart rate when a person exercises at a constant exercise intensity not less than $HR_{CP}$, and $t_{nlim}$ be a maximum duration when a person exercises at the constant exercise intensity, the relation is represented by one of equations (F) and (G) when P>CP, and represented by one of equations (H) and (I) when CP>P:

$$F_n = F_{n-1} - \frac{(HR - HR_{CP})}{(HR_n - HR_{CP})t_{n\,lim}}\Delta t + K(1 - F_{n-1})\frac{HR_{CP} - HR_{recovery}}{(HR_n - HR_{CP})t_{n\,lim}}\Delta t \qquad (F)$$

$$F_n = F_{n-1} - \frac{(HR - HR_{CP})}{\sum_{m=0}^{m=t_{n\,lim}/\Delta t}(HR_n - HR_{CP})}\Delta t + K(1 - F_{n-1})\frac{HR_{CP} - HR_{recovery}}{\sum_{m=0}^{m=t_{n\,lim}/\Delta t}(HR_n - HR_{CP})}\Delta t \qquad (G)$$

$$F_n = F_{n-1} + K(1 - F_{n-1})\frac{HR_{CP} - HR_{recovery}}{(HR_n - HR_{CP})t_{n\,lim}}\Delta t \qquad (H)$$

$$F_n = F_{n-1} + K(1 - F_{n-1})\frac{HR_{CP} - HR_{recovery}}{\sum_{m=0}^{m=t_{n\,lim}/\Delta t}(HR_n - HR_{CP})}\Delta t. \qquad (I)$$

7. A residual anaerobic work capacity calculating apparatus comprising:
 a heart rate obtaining unit configured to obtain a heart rate from a heart rate monitor; and
 an arithmetic unit configured to calculate a residual anaerobic work capacity based on a predetermined relationship between the residual anaerobic work capacity and the heart rate, and the heart rate obtained by the heart rate obtaining unit, the calculated residual anaerobic work capacity to manage biological information for a body performing anaerobic work, when said body is connected to said heart rate monitor by transmitting the calculated residual anaerobic work capacity to an external device or displaying the calculated residual anaerobic work capacity on a display to compare athletic abilities by using the calculated residual anaerobic work capacity.

8. The residual anaerobic work capacity calculating apparatus according to claim 7, wherein the arithmetic unit includes:
 a power calculator configured to calculate power based on a first relation indicating a relationship between the heart rate and the power, and the heart rate obtained by the heart rate obtaining unit; and
 a residual anaerobic work capacity calculator configured to calculate the residual anaerobic work capacity based on a second relation indicating a relationship between the power and the residual anaerobic work capacity, and the power calculated by the power calculator.

9. The residual anaerobic work capacity calculating apparatus according to claim 8, wherein, letting W'bal be the residual anaerobic work capacity, $W'_0$ be an anaerobic work capacity, t and u be time, $\tau$ be a time constant according to recovery of the anaerobic work capacity $W_0$, $W'_{EXP}$ be a consumed anaerobic work amount, P be power, CP be critical power, and $P_{avg}$ be an average value of the power when the power is not more than the critical power, the second relation includes equations (A), (B), (C), and (D):

$$W'bal = W_0 - \int_0^t W'_{EXP} e^{\frac{t-u}{\tau}} du \qquad (A)$$

$$W'_{EXP} = \begin{cases} P - CP & (P > CP) \\ 0 & (P \le CP) \end{cases} \qquad (B)$$

$$\tau = 546\exp(-0.01 D_{CP}) + 316 \qquad (C)$$

$$D_{CP} = CP - P_{avg}. \qquad (D)$$

10. The residual anaerobic work capacity calculating apparatus according to claim 7, wherein the arithmetic unit includes a residual anaerobic work capacity calculator configured to calculate a ratio of the residual anaerobic work capacity to an anaerobic work capacity based on a relation in which a relationship between the residual anaerobic work capacity and the power is standardized by the anaerobic work capacity, and the heart rate obtained by the heart rate obtaining unit.

11. The residual anaerobic work capacity calculating apparatus according to claim 10, wherein, letting F be the ratio of the residual anaerobic work capacity to the anaerobic work capacity, t and u (u<t) be time, Δt be a data interval, K be a coefficient according to recovery of an anaerobic work capacity $W_0$, $HR_{CP}$ be the heart rate when power is critical power, $HR_{recovery}$ be an average value of the heart rate when the power is not more than the critical power, $HR_n$ be the heart rate when a person exercises at a constant exercise intensity not less than $HR_{CP}$, and $t_{nlim}$ be a maximum duration when a person exercises at the constant exercise intensity, the relation is represented by one of equations (E) and (E'):

$$F(t) = 1 - (1 - F(u))e^{\frac{K(HR_{CP} - HR_{recovery})}{(HR_n - HR_{CP})t_{n\,lim}}(t-u)} \qquad (E)$$

$$F(t) = 1 - (1 - F(u))e^{\frac{K(HR_{CP} - HR_{recovery})}{\sum_{m=0}^{m=t_n\,lim/\Delta t}(HR_n - HR_{CP})}(t-u)} \qquad (E')$$

12. The residual anaerobic work capacity calculating apparatus according to claim 10, wherein, letting F be the ratio of the residual anaerobic work capacity to the anaerobic work capacity, t and u (u<t) be time, Δt be a data interval, K be a coefficient according to recovery of an anaerobic work capacity $W_0$, $HR_{CP}$ be the heart rate when power is critical power, $HR_{recovery}$ be an average value of the heart rate when the power is not more than the critical power, $HR_n$ be the heart rate when a person exercises at a constant exercise intensity not less than $HR_{CP}$, and $t_{nlim}$ be a maximum duration when a person exercises at the constant exercise intensity, the relation is represented by one of equations (F) and (G) when P>CP, and represented by one of equations (H) and (I) when CP>P:

$$F_n = F_{n-1} - \frac{(HR - HR_{CP})}{(HR_n - HR_{CP})t_{n\,lim}} \Delta t + K(1 - F_{n-1}) \frac{HR_{CP} - HR_{recovery}}{(HR_n - HR_{CP})t_{n\,lim}} \Delta t \qquad (F)$$

$$F_n = F_{n-1} - \frac{(HR - HR_{CP})}{\sum_{m=0}^{m=t_n\,lim/\Delta t}(HR_n - HR_{CP})} \Delta t + K(1 - F_{n-1}) \frac{HR_{CP} - HR_{recovery}}{\sum_{m=0}^{m=t_n\,lim/\Delta t}(HR_n - HR_{CP})} \Delta t \qquad (G)$$

$$F_n = F_{n-1} + K(1 - F_{n-1}) \frac{HR_{CP} - HR_{recovery}}{(HR_n - HR_{CP})t_{n\,lim}} \Delta t \qquad (H)$$

$$F_n = F_{n-1} + K(1 - F_{n-1}) \frac{HR_{CP} - HR_{recovery}}{\sum_{m=0}^{m=t_n\,lim/\Delta t}(HR_n - HR_{CP})} \Delta t. \qquad (I)$$

13. A residual anaerobic work capacity calculating apparatus comprising:
a memory configured to store a predetermined relationship between a residual anaerobic work capacity and a heart rate; and
a processor configured to obtain a heart rate, and calculate the residual anaerobic work capacity based on the obtained heart rate and the relationship stored in the memory, the calculated residual anaerobic work capacity to manage biological information for a body performing anaerobic work, when said body is connected to said heart rate monitor by transmitting the calculated residual anaerobic work capacity to an external device or displaying the calculated residual anaerobic work capacity on a display to compare athletic abilities by using the calculated residual anaerobic work capacity.

14. The residual anaerobic work capacity calculating apparatus according to claim 13, wherein
the memory is configured to store a first relation indicating a relationship between the heart rate and the power, and a second relation indicating a relationship between the power and the residual anaerobic work capacity, and
the processor is configured to calculate the power based on the obtained heart rate and the first relation stored in the memory, and calculate the residual anaerobic work capacity based on the calculated power and the second relation stored in the memory.

15. The residual anaerobic work capacity calculating apparatus according to claim 13, wherein
the memory is configured to store a relation in which a relationship between the residual anaerobic work capacity and power is standardized by an anaerobic work capacity, and
the processor is configured to calculate a ratio of the residual anaerobic work capacity to the anaerobic work capacity based on the obtained heart rate and the relation stored in the memory.

* * * * *